United States Patent
Mougin et al.

(10) Patent No.: US 6,318,149 B1
(45) Date of Patent: Nov. 20, 2001

(54) METHOD AND DEVICE FOR DETERMINING THE JOULE-THOMSON COEFFICIENT OF A FLUID

(75) Inventors: Pascal Mougin; Roxane Peumery, both of Rueil Malmaison; Gérard Moracchini, Andilly; José Sanchez, Viarmes, all of (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 09/550,203

(22) Filed: Apr. 17, 2000

(30) Foreign Application Priority Data

Apr. 23, 1999 (FR) .................................................. 99 05227

(51) Int. Cl.[7] .................................................. G01N 25/00
(52) U.S. Cl. ...................... 73/23.2; 73/25.01; 73/25.05; 73/31.04
(58) Field of Search ................................ 73/1.35, 31.04, 73/53.01, 61.78, 61.77, 61.73, 61.46, 61.47, 23.2, 25.01, 25.05

(56) References Cited

U.S. PATENT DOCUMENTS 5,415,024 * 5/1995 Proffitt et al. .......................... 73/61.46
5,980,102 * 11/1999 Stulen et al. .......................... 73/31.04

FOREIGN PATENT DOCUMENTS 0070188  1/1983  (EP) ................................ G01N/33/28
1732191  3/1983  (SU) ................................ G01K/17/00
777557  11/1981 (SU) ................................ G01N/15/08

OTHER PUBLICATIONS

Derwent Abstract No. 1982–B4643E of SU 827866B to Tsvetnov.*
Atkins, P. W. Physical Chemistry. Oxford University Press, 1986, pp. 66–67.*

* cited by examiner

Primary Examiner—Daniel S. Larkin
Assistant Examiner—Michael Cygan
(74) Attorney, Agent, or Firm—Antonelli, Terry, Stout & Kraus, LLP

(57) ABSTRACT

The invention is a method for determining the Joule-Thomson coefficient of a fluid, expressing the temperature variation in relation to a pressure variation thereof. The fluid is injected at a determined injection temperature into a thin tube (8) (preferably a capillary tube in order to obtain a high pressure drop with reasonable flow rates) which contains a temperature detector (TC1) leading to a pressure drop for the fluid. The temperature variation of the fluid in relation to the injection temperature is measured by means of this temperature detector. The pressure drop undergone by the fluid in tube (8), due to the presence of this temperature detector, is also measured and the Joule-Thomson coefficient is calculated by combination of measurements of the pressure drop and of the temperature variation of the fluid. The method can be applied notably in the field of hydrocarbon production, more particularly hydrocarbons coming from high-pressure and high-temperature reservoirs and in gas lines.

30 Claims, 4 Drawing Sheets

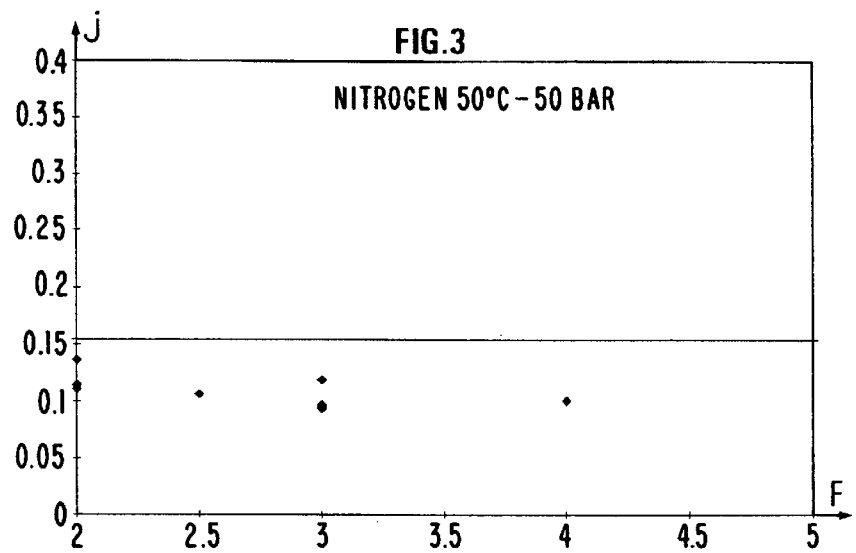
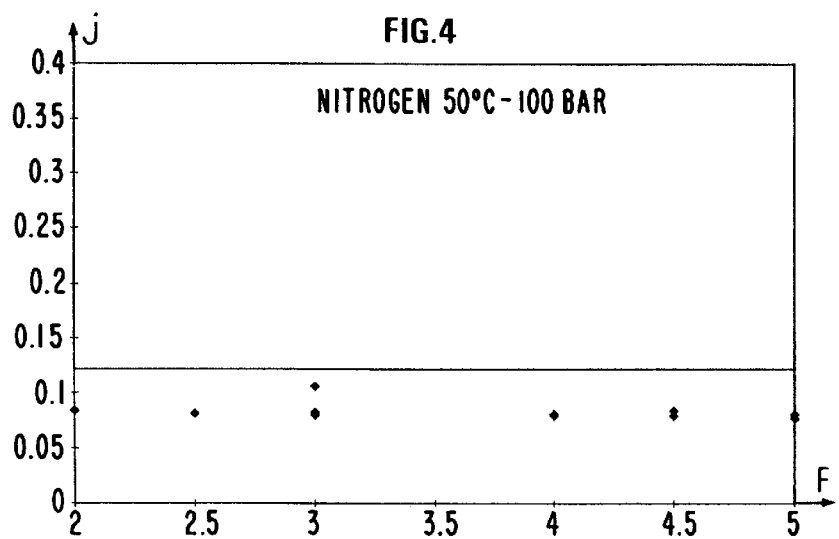
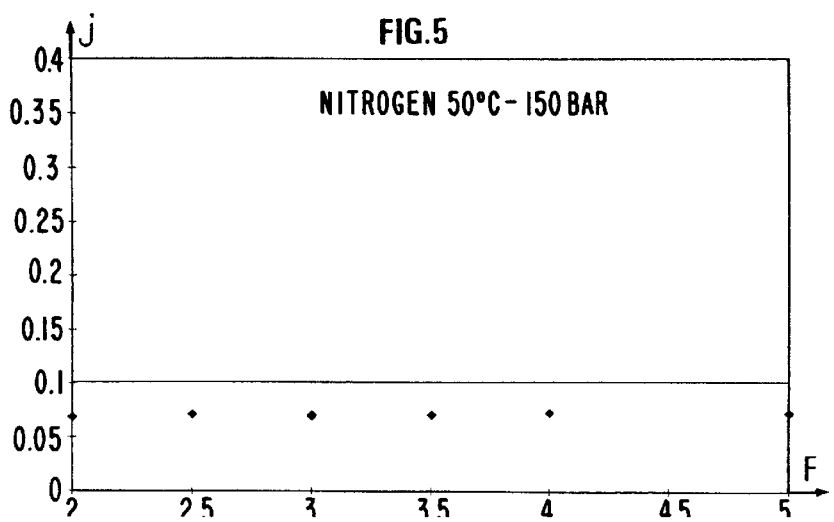

METHOD AND DEVICE FOR DETERMINING THE JOULE-THOMSON COEFFICIENT OF A FLUID

BACKGROUND OF THE INVENTION

1. Field of the Invention

The present invention relates to a method and to a device for measuring Joule-Thomson coefficients of fluids.

2. Description of the Prior Art

The Joule-Thomson coefficient $\mu$ measures the temperature variation of a fluid subjected to a pressure drop in an isenthalpic situation.

$$\mu = \left(\frac{\partial T}{\partial T}\right)_H$$

This isenthalpy condition is precisely the one that is encountered during expansion of a fluid in a valve or in a line provided that the energy which is dissipated from the fluid can be disregarded.

Precise measurement of the Joule-Thomson coefficient finds applications in many fields where carrying fluids in pipes leads to changes of state that affect the proper circulation thereof, notably in the field of high-pressure/high-temperature (HP-HT) hydrocarbon reservoir production. This measurement allows determination of the << thermal profile>>in all the energy dissipative elements.

According to the temperature and pressure conditions, the Joule-Thomson coefficient $\mu$ can be positive or negative, as shown in FIG. 1. In the case of a positive coefficient ($\mu$>0), the gas cools down during an expansion whereas a negative coefficient ($\mu$<0) leads to warming through expansion. The positive range of the coefficient is separated from the negative range by inversion curve IC. It can be seen that, under the HP-HT conditions prevailing in a well at a great depth, coefficient $\mu$ is negative: the fluid warms up through expansion. This is observed at the present time in reservoir production wells situated at a relatively great depth, notably in certain wells in the North Sea producing condensate gases where the HP-HT conditions cause an inversion of the Joule-Thomson coefficient.

The sign and the value of the Joule-Thomson coefficient are therefore important for dimensioning of a production well since it influences the thermal profile of the production facilities. In the case of a negative coefficient, it is imperative to know the warming reached through expansion: selection of the building materials depends thereon. This coefficient can also be used for dimensioning gas lines, for the same reasons. It is also necessary to know the sign and the value of this coefficient in order to assess the risks of hydrate or paraffin formation in case of a temperature decrease through expansion, so as to be able to select the suitable technique allowing prevention of the formation of deposits in the lines.

There are many reference books in the literature showing how to calculate the inversion curve IC(P,T) of the Joule-Thomson coefficient by means of equations of state conventionally used in the petroleum industry. One can notably refer to:

Kortekaas W. G., et al; Joule-Thomson Expansion of High-Pressure-High-Temperature Gas Condensates, in Fluid Phase Equilibria, 139, 1997, p.207–218.

However, this approach is difficult to exploit in practice for lack of the necessary experimental data which are scarcely disclosed. Furthermore, measuring the Joule-Thomson coefficient $\mu$ is delicate because very low absolute values of the order of some tenths ° C./bar (some ° C./MPa) are assessed. Good determination of the inversion curve IC requires great precision because the observable temperature difference is very close to 0.

There are different types of experimental devices allowing determination of the Joule-Thomson coefficient by measuring the temperature variation of a fluid flowing through an element.

According to a first embodiment, this element consists of a porous medium causing a pressure drop that is a function of its permeability and of the fluid flow rate. Such a device has many drawbacks insofar as the Joule-Thomson effect is dispersed in the whole porous volume that is difficult to insulate thermally, and it has a certain thermal inertia, which requires a large amount of fluid in order to reach the state of thermal equilibrium during measurement.

According to a second embodiment, the element causing a pressure drop consists of a valve. This is an advantageous solution because, in this case, the pressure difference between the inlet and the outlet of the device can be readily varied. Furthermore, the Joule-Thomson effect is rather localized, but the various parts of the device such as the seat, the needle, etc., however form a thermal mass producing thermal losses that are difficult to prevent.

Assurance of a good thermal insulation and of a good localization of the Joule-Thomson effect are the key factors of a good measurement. These are the qualities of the device according to the invention.

SUMMARY OF THE INVENTION

The method according to the invention allows determination of the Joule-Thomson coefficient of a fluid by combination of measurements of concomitant pressure and temperature variations of a circulating fluid. It comprises injecting this fluid at a determined temperature into a thin tube containing a temperature detector leading to a pressure drop for this fluid, measuring, by means of this detector, the temperature variation of the fluid in relation to its injection temperature, measuring the pressure drop undergone by the fluid and determining the Joule-Thomson coefficient by combination of the pressure drop and temperature variation measurements of the fluid. The fine tube is preferably thermally confined in order to avoid heat losses.

The device according to the invention allows determination of the Joule-Thomson coefficient of a fluid under pressure. It comprises a tube, means for injecting the fluid into the tube at a determined temperature, a first detector in the tube creating a pressure drop and suited to measure the temperature variation of the fluid that has undergone this pressure drop, pressure detectors upstream and downstream from the tube for measuring the pressure drop, a second detector for measuring the temperature of the fluid injected, and a calculation means allowing determination of the Joule-Thomson coefficient of the fluid from this pressure drop and from this temperature variation.

The device preferably comprises confinement means for thermal insulation of the fine tube, comprising for example a confinement tube containing the fine tube, this confinement tube being provided with terminal parts at the two opposite ends thereof defining a sealed enclosure therewith, channels in the terminal parts allowing communication of the inside of the tube with the fluid injection means, the inside of the confinement tube with means for evacuating the tube, and the tube with the pressure means.

According to an embodiment, the confinement means further comprise an intermediate tube between the fine tube and the confinement tube. At least one of the tubes around the fine tube is provided with a reflective coating on the inner wall thereof in order to prevent heat losses through radiation.

The device preferably comprises a unit intended for temperature conditioning of the fluid prior to the injection thereof.

The temperature detectors are preferably identical thermocouples connected in opposition so as to detect slight temperature variations.

Using a flow valve for controlling the outgoing flow allows checking that measurement of the Joule-Thomson coefficient is really independent of the flow rate.

Highly localized measurement at the end of the pressure drop zone in the fine tube, preferably combined with good confinement of the fine tube substantially prevents any heat loss in the measurement zone, guarantees very high accuracy.

BRIEF DESCRIPTION OF THE DRAWINGS

Other features and advantages of the device according to the invention will be clear from reading the description hereafter of a non limitative example of the device, with reference to the accompanying drawings wherein:

FIGS. 2A, 2B are sectional views of terminal parts 2A and 2B respectively, FIGS. 3 to 5 show experimental measurements of the variations of the Joule-Thomson coefficient J of nitrogen as a function of the flow rate F respectively for pressures of 5, 10 and 15 MPa obtained by means of the device and, by way of comparison, values J1 to J3 obtained by calculation from the specific equation of state of this gas for the same pressures respectively, and FIG. 6 diagrammatically shows an overall view of the device in its thermostat-controlled enclosure.

DETAILED DESCRIPTION OF THE PREFERRED EMBODIMENTS OF THE INVENTION

Figure 1:
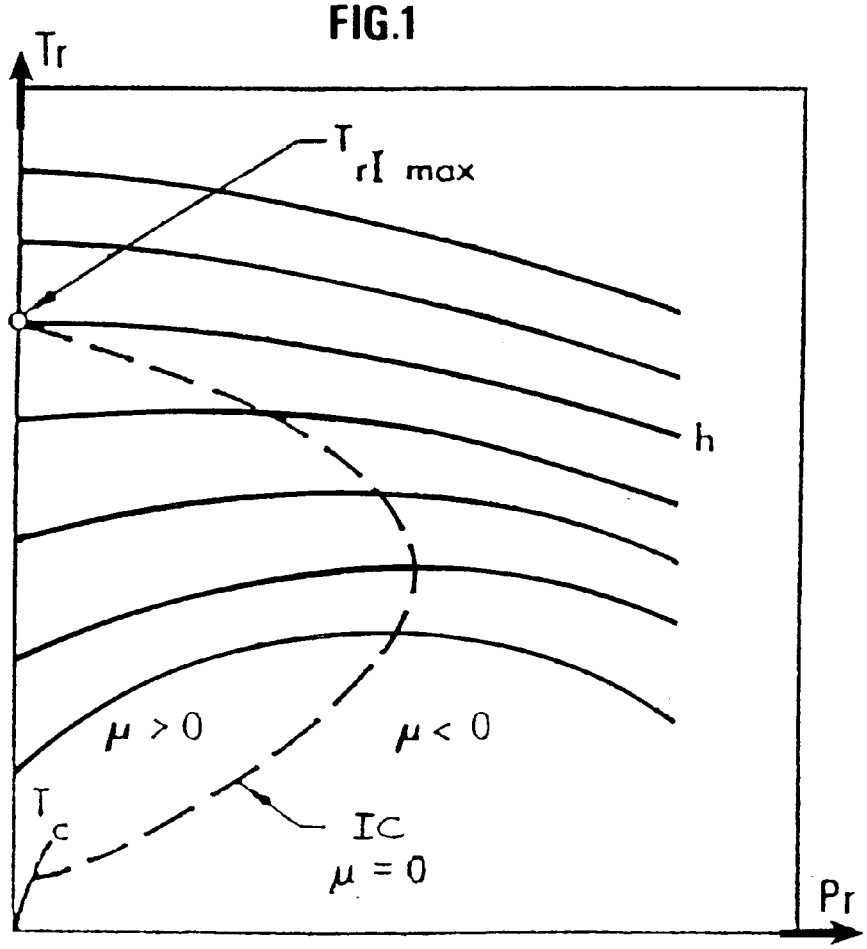
FIG. 1 shows a network of variation curves, at constant enthalpy, of the temperature Tr of a fluid as a function of its pressure Pr.
Figure 2:
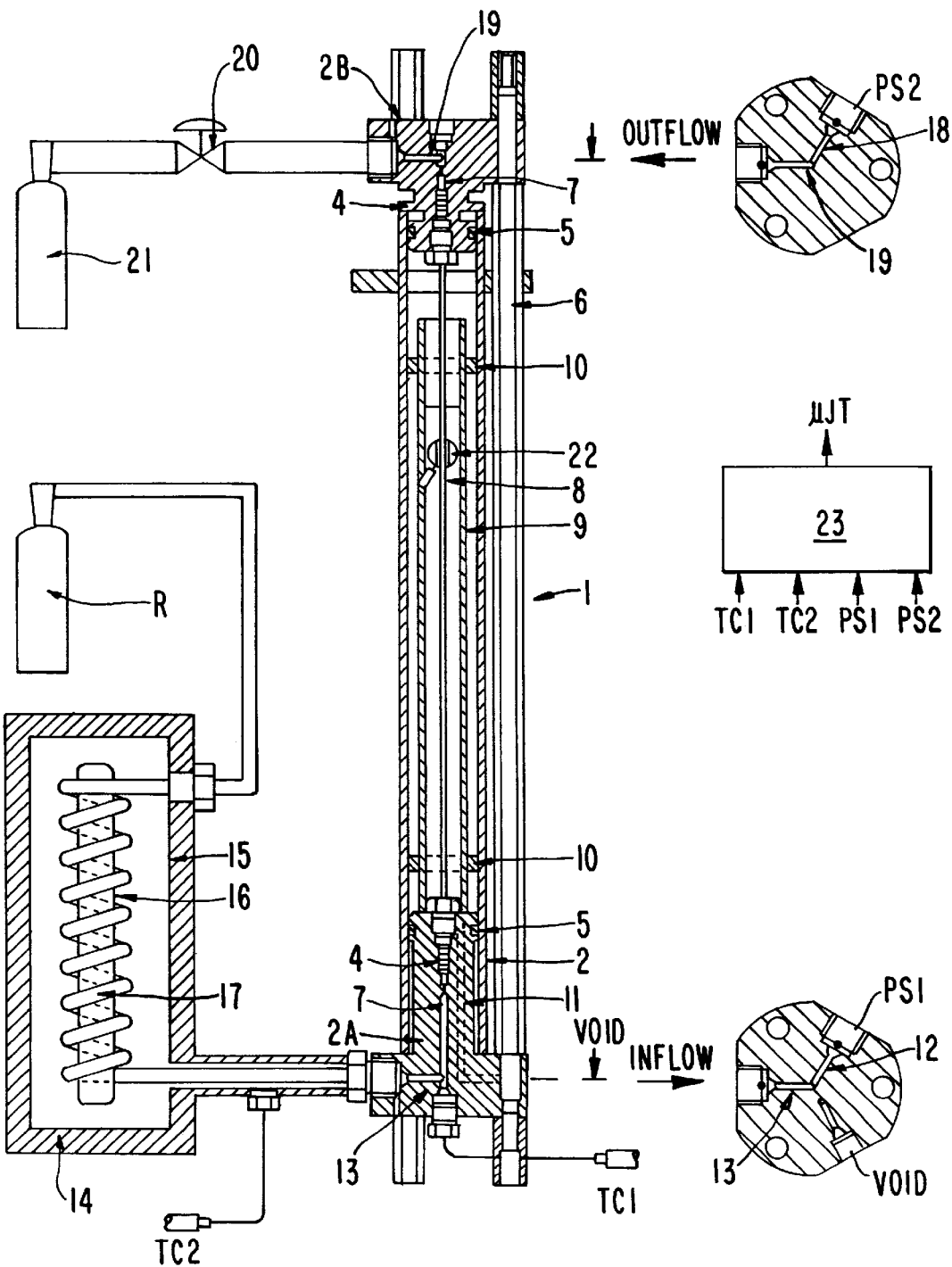
FIG. 2 is a cross-sectional view of the device.

The device comprises (FIG. 2) a measuring unit 1. It includes an outer tube 2 preferably internally coated with a reflective metal layer. The outer tube is associated with two terminal parts 2A, 2B hereafter referred to as upstream terminal part and downstream terminal part respectively. Each one comprises a cylindrical extension 4 whose diameter is suited to the inside diameter of tube 2, externally provided with an annular seal 5. The two terminal parts 2A, 2B are connected by a cross member 6 associated with fastening means that are not shown. Each terminal part comprises an axial channel 7.

The respective axial channels of terminal parts 2A, 2B are connected by a fine metal tube 8. An intermediate tube 9 is arranged around fine tube 8. The intermediate tube 9 is positioned in relation to outer tube 2 by means of plastic rings 10. This intermediate tube 9 is for example made of glass and it can be internally coated with a reflective metal layer such as a silver coating. A channel 11 is provided through upstream terminal part 2A. It opens into intermediate tube 9 and communicates externally with a vacuum pump P. The combined action of the silver coating on the inner wall of outer tube 2 and of the vacuum prevailing during operation inside tubes 2 and 9 allows limiting to a minimum the heat losses due to conduction and radiation.

The axial channel 7 in upstream part 2A communicates through a first radial channel 12 with a first pressure detector PSI and, through a second radial channel 13, with fluid injection means R by means of a temperature stabilization unit 14. This unit comprises for example a thermostat-controlled enclosure 15 connected to measuring unit 1. This enclosure 15 contains a heat exchanger comprising for example a copper coil 16 on which a fine tube 17 (a capillary tube for example intended for delivery of the fluid to be studied) is tightly wound. Copper coil 16 can remain empty and passively transmit the temperature of the enclosure to gas delivery tube 17, or it can be connected to a primary circuit (not shown) in which a heated fluid circulates.

The axial channel 7 in downstream part 2B communicates, through a first radial channel 18, with a pressure detector PS2 and, through a second channel 19, either directly with the outside (free exhaust) or, if the measured fluid is to be recovered for other measurements (for example for measuring the reservoir fluid generally available in limited amount), with a fluid recovery chamber 21, by means of a precise flow control valve 20, of micrometric screw type for example.

A first temperature detector, in this case a first thermocouple TC1, is introduced into fine tube 8, over part of its length, through axial channel 7 in upstream part 2A. A second thermocouple TC2 is placed in the zone connecting temperature stabilization unit 14 to measuring unit 1. The two thermocouples are identical. They come from the same wire coils and are connected in opposition in order to better detect slight temperature variations.

The presence of first thermocouple TC1 in fine tube 8 creates a pressure drop distributed over a well-determined distance, which depends on the annular space remaining around the detector. The section of fine tube 8 is selected according to the diameter of thermocouple TC1 so as to obtain a high pressure drop with reasonable flow rates, considering the gas availability. The temperature variation of the fluid, correlated with the pressure drop caused by thermocouple TC1, is measured at the end 22 thereof Measurements are performed in steady state. Once temperature conditioning unit 14 has reached a stable working temperature, a source R for injecting a fluid under pressure, such as a gas bottle, is connected thereto. After reheating by means of temperature exchanger 16, the fluid under pressure flows into the axial channel 7 of terminal part 2A and fine tube 8. Its temperature, either increased or decreased in relation to the temperature prevailing in conditioning unit 14, is measured by first thermocouple TC1 at the end 22 thereof The measuring signals of the two thermocouples TC1, TC2 and the upstream and downstream pressure measurements obtained by pressure detectors PS1, PS2 are applied to a computer 23 which deduces the Joule-Thomson coefficient therefrom.

Tests have been carried out to validate the measurements provided by the device according to the invention. Nitrogen was successively injected at various pressures precisely determined (by means of an expansion valve, not shown, at the outlet of gas bottle R) 5 MPa, 10 MPa and 15 MPa. At each one of these stabilized pressures, several Joule-Thomson coefficient measurements were performed by precisely modifying the flow rate by means of valve 20. By way of comparison, the corresponding theoretical values J1, J2, J3 of this coefficient were determined from a specific equation of state of this gas for the same pressures. As can be seen in FIGS. 3 to 5, the results obtained with the device according to the invention, in all the experimental cases, are entirely in accordance with the theoretical values. They are really independent of the flow rate of the fluid and therefore of its kinetic energy, as can be checked by using valve 20.

Figure 6:
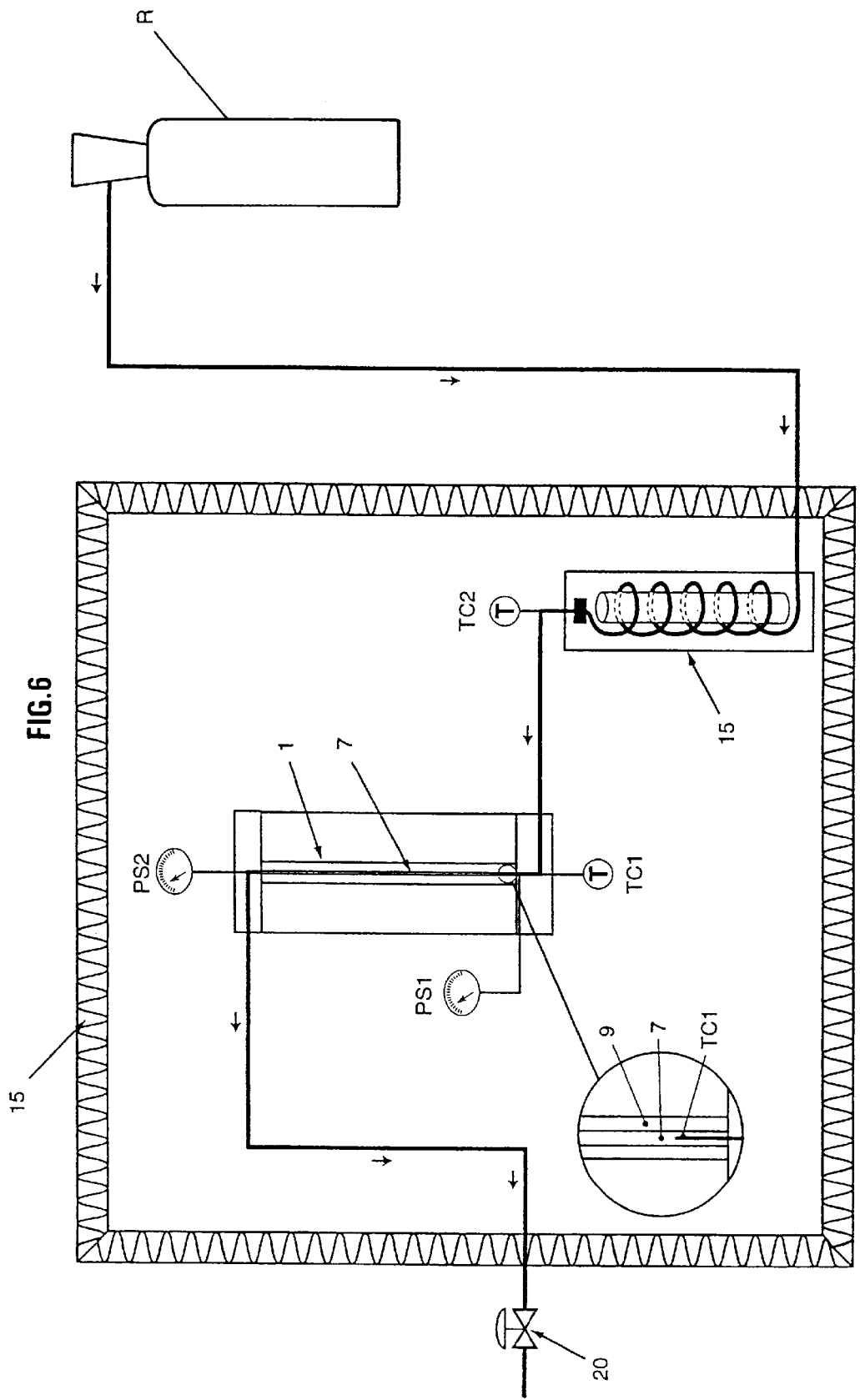

FIG. 6 illustrates the invention positioned in a thermostatically controlled enclosure.

What is claimed is:

1. A method for determining the Joule-Thomson coefficient of a fluid, by combining measurements of concomitant pressure and temperature variations undergone by a circulating fluid, comprising:
   injecting the fluid at a determined injection temperature into a tube containing a temperature detector which causes a pressure drop in the fluid;
   measuring a temperature variation of the fluid in relation to an injection temperature of the fluid with the temperature detector;
   measuring the pressure drop undergone by the fluid; and
   calculating the Joule-Thomson coefficient by combining measurements of the pressure drop and of the temperature variation undergone by the fluid.

2. A method as claimed in claim 1, wherein:
   the tube wherein the temperature is measured is thermally insulated.

3. A device for determining the Joule-Thomson coefficient of a fluid under pressure by combining measurements of concomitant pressure and temperature variations undergone by a circulating fluid, comprising:
   a first tube;
   a fluid source providing fluid injected into the first tube at a determined temperature;
   a first detector in the first tube which creates a pressure drop and measures a temperature variation of the fluid that has undergone the pressure drop;
   pressure detectors respectively positioned upstream and downstream from the first tube which measure the pressure drop;
   a second detector which measures a temperature of the fluid provided from the fluid source; and
   another device which determines the Joule-Thomson coefficient of the fluid from the measured pressure drop and from the measured temperature variation.

4. A device in accordance with claim 3 wherein:
   the another device is a computer.

5. A device as claimed in claim 3, comprising:
   a confinement including thermal insulation.

6. A device as claimed in claim 1, comprising:
   a confinement including thermal insulation.

7. A device as claimed in claim 5, wherein:
   the confinement includes a confinement tube containing the first tube; and
   the confinement tube comprises terminal parts at opposite ends thereof, defining a sealed enclosure therewith and channels in the terminal parts which provide communication of an inside of the first tube with a fluid source, communication of the confinement to a vacuum source, and communication of the first tube to the pressure detectors.

8. A device as claimed in claim 5, wherein:
   the confinement includes a confinement tube containing the first tube; and
   the confinement tube comprises terminal parts at opposite ends thereof, defining a sealed enclosure therewith and channels in the terminal parts which provide communication of an inside of the first tube with a fluid source, communication of the confinement to a vacuum source, and communication of the first tube to the pressure detectors.

9. A device as claimed in claim 7, wherein:
   the confinement further comprises an intermediate tube between the first tube and the confinement tube.

10. A device as claimed in claim 3 wherein:
    at least one other tube containing the first tube is internally coated with a reflective layer to reflect heat therefrom.

11. A device as claimed in claim 4 wherein:
    at least one other tube containing the tube is internally coated with a reflective layer to reflect heat therefrom.

12. A device as claimed in claim 5 wherein:
    at least one other tube containing the tube is internally coated with a reflective layer to reflect heat therefrom.

13. A device as claimed in claim 6 wherein:
    at least one other tube containing the tube is internally coated with a reflective layer to reflect heat therefrom.

14. A device as claimed in claim 7 wherein:
    at least one other tube containing the tube is internally coated with a reflective layer to reflect heat therefrom.

15. A device as claimed in claim 8 wherein:
    at least one other tube containing the tube is internally coated with a reflective layer to reflect heat therefrom.

16. A device as claimed in claim 3 comprising:
    a temperature control which controls a temperature of the fluid injected into the first tube.

17. A device as claimed in claim 4 comprising:
    a temperature control which controls a temperature of the fluid injected into the first tube.

18. A device as claimed in claim 5 comprising:
    a temperature control which controls a temperature of the fluid injected into the first tube.

19. A device as claimed in claim 6 comprising:
    a temperature control which controls a temperature of the fluid injected into the first tube.

20. A device as claimed in claim 7 comprising:
    a temperature control which controls a temperature of the fluid injected into the first tube.

21. A device as claimed in claim 8 comprising:
    a temperature control which controls a temperature of the fluid injected into the first tube.

22. A device as claimed in claim 9 comprising:
    a temperature control which controls a temperature of the fluid injected into the first tube.

23. A device as claimed in claim 10 comprising:
    a temperature control which controls a temperature of the fluid injected into the first tube.

24. A device as claimed in claim 11 comprising:
    a temperature control which controls a temperature of the fluid injected into the first tube.

25. A device as claimed in claim 12 comprising:
    a temperature control which controls a temperature of the fluid injected into the first tube.

26. A device as claimed in claim 13 comprising:
    a temperature control which controls a temperature of the fluid injected into the first tube.

27. A device as claimed in claim 14 comprising:
    a temperature control which controls a temperature of the fluid injected into the first tube.

28. A device as claimed in claim 15 comprising:
    a temperature control which controls a temperature of the fluid injected into the first tube.

29. A device as claimed in claim 3, wherein:
    the temperature detectors are identical thermocouples connected in opposition.

30. A device as claimed in claim 3, comprising:
    a valve which controls a flow rate of the fluid flowing from the downstream pressure detector.

* * * * *